United States Patent
Buchnik et al.

(10) Patent No.: US 12,299,783 B2
(45) Date of Patent: May 13, 2025

(54) PHACOEMULSIFATION GUIDANCE

(71) Applicant: JOHNSON & JOHNSON SURGICAL VISION, INC., Irvine, CA (US)

(72) Inventors: Yael Buchnik, Adi (IL); Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 431 days.

(21) Appl. No.: 17/740,675

(22) Filed: May 10, 2022

(65) Prior Publication Data
US 2023/0368441 A1    Nov. 16, 2023

(51) Int. Cl.
| | |
|---|---|
| G06T 11/00 | (2006.01) |
| A61B 3/10 | (2006.01) |
| A61B 34/10 | (2016.01) |
| A61F 9/007 | (2006.01) |
| G06T 3/60 | (2024.01) |
| G06T 7/00 | (2017.01) |
| G06T 7/30 | (2017.01) |
| G06T 7/68 | (2017.01) |

(52) U.S. Cl.
CPC ............ *G06T 11/008* (2013.01); *A61B 34/10* (2016.02); *G06T 3/60* (2013.01); *G06T 7/0012* (2013.01); *G06T 7/30* (2017.01); *G06T 7/68* (2017.01); *A61B 3/102* (2013.01); *A61B 2034/104* (2016.02); *A61B 2034/105* (2016.02); *A61F 9/00745* (2013.01); *G06T 2207/10101* (2013.01); *G06T 2207/30041* (2013.01)

(58) Field of Classification Search
CPC ....... G06T 11/008; G06T 3/60; G06T 7/0012; G06T 7/30; G06T 7/68; G06T 2207/10101; G06T 2207/30041; A61B 34/10; A61B 3/102; A61B 2034/104; A61B 2034/105; A61F 9/00745
See application file for complete search history.

(56) References Cited

U.S. PATENT DOCUMENTS

| | | | |
|---|---|---|---|
| 8,945,140 B2 | 2/2015 | Hubschman et al. | |
| 9,278,028 B2 * | 3/2016 | Friedman | A61F 9/00825 |
| 9,384,582 B2 * | 7/2016 | Izatt | G01B 11/2441 |
| 9,560,965 B2 * | 2/2017 | Schuhrke | G06T 7/74 |

(Continued)

OTHER PUBLICATIONS

Posarelli, Chiara et al. "What Is the Impact of Intraoperative Microscope-Integrated OCT in Ophthalmic Surgery? Relevant Applications and Outcomes. A Systematic Review." Journal of clinical medicine vol. 9,6 1682. Jun. 2, 2020.

(Continued)

*Primary Examiner* — Ian L Lemieux
*Assistant Examiner* — Sebastian-Sy Vuchi Ngo (57) ABSTRACT

A phacoemulsification system having an imaging device configured to capture images of an eye and a phacoemulsification probe, a display, and a processor configured to receive an eye scan result providing a two-dimensional array of cataract thicknesses of the eye, find cutlines through which to cut the cataract into sections responsively to the two-dimensional array of cataract thicknesses, and render the images of the eye and the phacoemulsification probe with representations of the found cutlines through which to cut the cataract into sections to the display.

25 Claims, 4 Drawing Sheets

(56) References Cited

U.S. PATENT DOCUMENTS

| | | | | |
|---|---|---|---|---|
| 11,615,526 | B2* | 3/2023 | Loerner | A61F 9/00836 |
| | | | | 382/128 |
| 11,998,486 | B2* | 6/2024 | Palanker | A61F 9/0084 |
| 2010/0324542 | A1* | 12/2010 | Kurtz | A61F 9/00825 |
| | | | | 606/6 |
| 2012/0022546 | A1* | 1/2012 | Hubschman | A61F 9/00754 |
| | | | | 606/107 |
| 2012/0262720 | A1 | 10/2012 | Brown et al. | |
| 2015/0031993 | A1 | 1/2015 | Buckland et al. | |
| 2016/0106588 | A1 | 4/2016 | Srinivasan et al. | |
| 2016/0296375 | A1* | 10/2016 | Reich | A61F 9/00825 |
| 2022/0386864 | A1* | 12/2022 | Higuchi | A61B 3/0058 |
| 2023/0210692 | A1* | 7/2023 | Casutt | A61F 9/00745 |
| | | | | 604/22 |

OTHER PUBLICATIONS

Pakuliene, G., Zimarinas, K., Nedzelskiene, I. et al. Anterior segment optical coherence tomography imaging and ocular biometry in cataract patients with open angle glaucoma comorbidity. BMC Ophthalmol 21, 127 (2021).

Almutlak MA, Aloniazan T, May W. Real-time Optical Coherence Tomography Incorporated in the Operating Microscope during Cataract Surgery. Middle East Afr J Ophthalmol. 2017;24(3):156-158.

Conni Bergmann Koury, Precision, integration, efficiency: Sweet cataract suites Interconnected devices in the OR help surgeons meet and exceed patients' refractive goals., Ophthalmology Management, vol. 23, Issue: Dec. 2019, pp. 35, 36, 39, 55.

Martinez-Enriquez E, Sun M, Velasco-Ocana M, Birkenfeld J, Pérez-Merino P, Marcos S. Optical Coherence Tomography Based Estimates of Crystalline Lens Volume, Equatorial Diameter, and Plane Position. Invest Ophthalmol Vis Sci. Jul. 1, 2016;57(9):OCT600-10.

Martinez-Enriquez E., et al., "Optical Coherence Tomography Based Estimates of Crystalline Lens Volume, Equatorial Diameter, and Plane Position," Investigative Ophthalmology & Visual Science, 2016, vol. 57(9), pp. OCT600-10.

* cited by examiner

PHACOEMULSIFICATION GUIDANCE

FIELD OF THE DISCLOSURE

The present disclosure relates to medical systems, and in particular, but not exclusively, to phacoemulsification procedures.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Then a small incision is made in the cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract, while a pump device aspirates particles from the cataract through the tip. The pump is typically controlled with a microprocessor. The pump may be a flow-based pump, e.g., peristaltic and/or a vacuum-based pump, e.g., venturi type of pump. Aspirated fluids are replaced with irrigation of a balanced salt solution to maintain the anterior chamber of the eye. After removing the cataract with phacoemulsification, the softer outer lens cortex is removed with suction. An intraocular lens (IOL) is introduced into the empty lens capsule. Small struts called haptics help hold the IOL in place. Once correctly implanted the IOL restores the patient's vision.

BRIEF DESCRIPTION OF THE DRAWINGS

The present disclosure will be understood from the following detailed description, taken in conjunction with the drawings in which.

DESCRIPTION OF EXAMPLES

Overview

As previously mentioned, as part of a phacoemulsification procedure the cataract is emulsified using an ultrasound driven needle. It is very difficult to remove hard cataracts. Another problem is that the use of the ultrasound driven needle creates heat in the eye which could damage structures of the eye. Therefore, it is important to minimize the emulsification work as much as possible to limit the amount of heat generated in the eye.

One solution is to divide the cataract into quarters and then use a divide and conquer technique to emulsify the cataract one quarter at a time. However, due to the hardness of the cataract this divide and conquer technique may also be challenging leading to the risks of prolonged emulsification, including heating and damage.

In some exemplary modes, a system is provided which analyses the thicknesses of the cataract and finds a most suitable way to divide the cataract to minimize emulsification effort and time and therefore generate less heat. It is assumed that starting emulsification with the thinnest regions of the cataract leads to a quicker emulsification as the thinnest regions provide the weakest links of the cataract. Using an optimization algorithm (e.g., optimizing thinness over length) the cataract is divided into sections. The division of the cataract may be indicated (e.g., using lines) over an image (e.g., live video) of the cataract captured by an imaging device (e.g., a camera). In some exemplary modes the cataract is divided into section (e.g., quarters), using two intersecting, substantially perpendicular lines (i.e., within 5 degrees of being exactly perpendicular).

In some exemplary modes, a scanning device performs an eye scan and generates an eye scan result. In some exemplary modes, the eye scan result is a result derived from an anterior segment optical coherence tomography (AS-OCT) scan. The eye scan result provides a two-dimensional array of cataract thicknesses of the eye. For example, the eye scan result may include thickness values of the cataract for different x and y coordinate combinations or in any suitable coordinate system (e.g., a polar coordinate system) as measured in a direction from the front to the back of the eye and may be derived from the eye scan result (e.g., AS-OCT scan).

The system finds cutlines through which to cut the cataract into sections responsively to the two-dimensional array of cataract thicknesses. In some exemplary modes, the system finds cutlines providing a minimum thickness measurement responsively to values of the two-dimensional array through which the cutlines traverse. For example, the system may find cutlines including the maximum number of thickness values below a given thickness values, e.g., below 2 or 3 units of thickness. The units of thickness may be any suitable unit of thickness such as a distance from the front of the cataract to the back of the cataract (e.g., measured in millimeters) or may be a coefficient which includes distance from the front of the cataract to the back of the cataract and density, such as an integral of dt multiplied by dD, where t is thickness, and D is density. The OCT provides the amount of light, which was refracted from the cataract, which is directly proportional to distance from the front of the cataract to the back of the cataract and the density of the cataract.

In some exemplary modes, the system finds cutlines which provide a minimum summation of the values of the two-dimensional array through which the cutlines traverse. For example, if a line passes through thickness values 1, 2, 2, 3, 4, 1 then the thickness measurement of that line is equal to 13.

In some exemplary modes, the system rotates an arrangement of lines (e.g., two intersecting perpendicular lines) around a point in the two-dimensional array to find an orientation of the arrangement which provides the minimum thickness measurement responsively to the values of the two-dimensional array through with the lines of the arrangement traverse. The orientation of the arrangement which provides the minimum thickness measurement defines the cutlines.

The system renders live images (e.g., a video) of the eye and the phacoemulsification probe with representations of the found cutlines (superimposed over the images of the eye) through which to cut the cataract into sections to the display. The section divisions are shown as lines (e.g., solid or broken lines) over the image of the eye and probe on the display (as shown above). The physician then starts cutting the cataract at the lines (that indicate the thinnest regions of the cataract) thereby providing an easier and quicker emulsification of the cataract.

System Description

Figure 1:
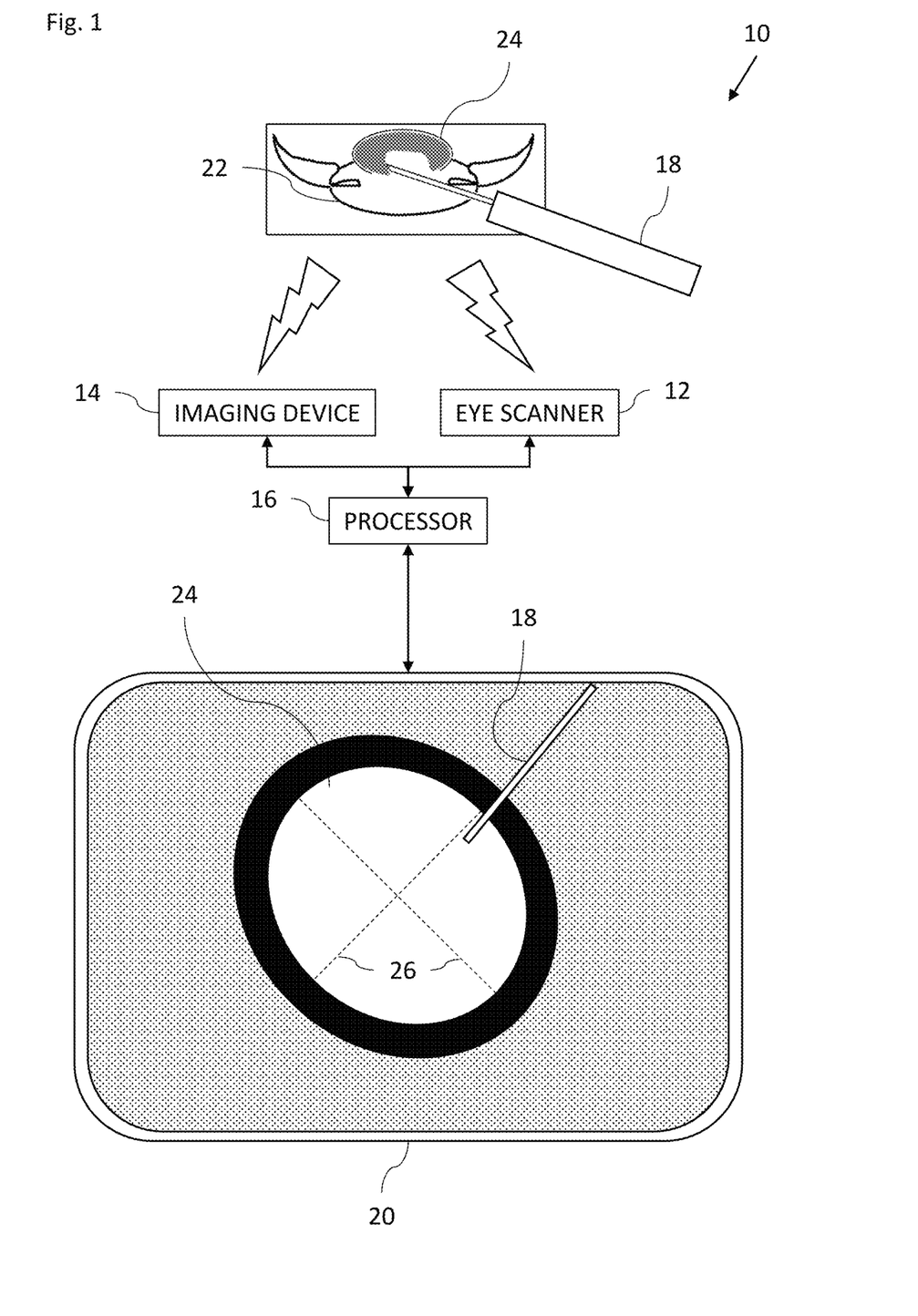
FIG. 1 is a partly pictorial, partly block diagram view of phacoemulsification system constructed and operative in accordance with an exemplary mode of the present disclosure.

Reference is now made to FIG. 1 is a partly pictorial, partly block diagram view of phacoemulsification system 10 constructed and operative in accordance with an exemplary mode of the present disclosure. The system 10 includes an eye scanner 12, an imaging device 14, a processor 16, a phacoemulsification probe 18, and a display 20 (e.g., a phaco-graphical user interface or a surgical microscope).

The eye scanner 12 is configured to perform an eye scan of an eye 22 and generate an eye scan result. In some exemplary modes, the eye scan result is a result derived from an anterior segment optical coherence tomography (AS-OCT) scan. The imaging device 14 is configured to capture images (e.g., a series of still images or a video) of the eye 22 and the phacoemulsification probe 18. FIG. 1 shows an image of the eye 22 and the phacoemulsification probe 18 captured by the imaging device 14 with representations 26 (shown as dotted lines) of cutlines (superimposed thereon) through which to cut a cataract 24 of the eye 22 with the phacoemulsification probe 18.

Figure 2:
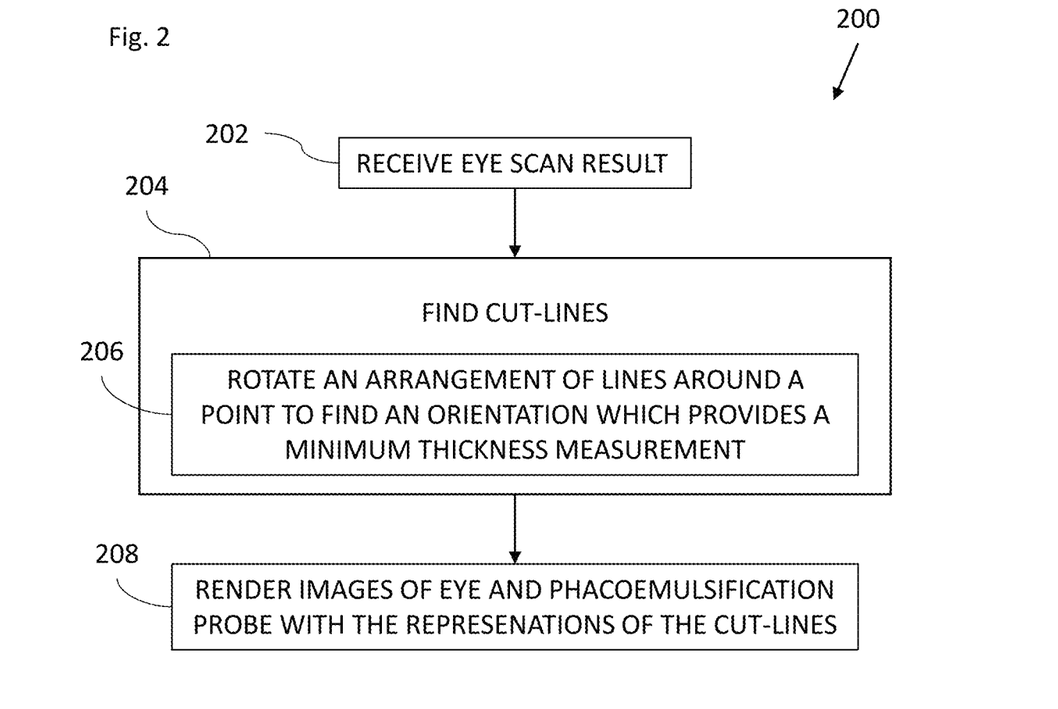
FIG. 2 is a flowchart including steps in a method of operation of the system of FIG. 1.

Reference is now made to FIG. 2, which is a flowchart 200 including steps in a method of operation of the system 10 of FIG. 1. In overview, an eye scan result is received (e.g., from the eye scanner 12) (block 202) and processed by the processor 16 to find cutlines which minimize the cutting effort through the cataract (block 204). The cutting effort is assumed to be minimized by finding the thinnest regions of the cataract to cut through. The cutlines are rendered by the processor 16 in the display 20 over live images of the eye 22 and the phacoemulsification probe 18 captured by the imaging device 14 (block 208).

The method shown in FIG. 2 is now described in more detail. The processor 16 is configured to receive the eye scan result (from the eye scanner 12) providing a two-dimensional array of cataract thicknesses of the eye. The eye scanner 12 typically performs the scan of the eye prior to the surgery.

Figure 3:
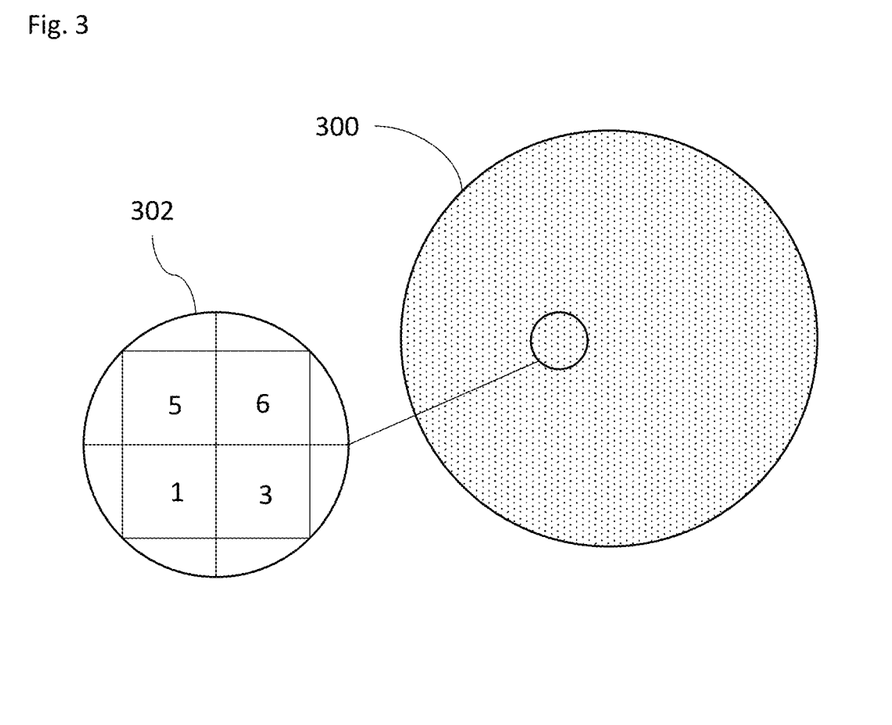
FIG. 3 is a schematic view of an example of an eye scan result.

Reference is now made to FIG. 3, which is a schematic view of an example of an eye scan result 300. The eye scan result 300 includes a two-dimensional array of cataract thickness of the eye 22. For example, the eye scan result 300 may include thickness values for different x and y coordinate combinations or coordinate combinations in any suitable coordinate system (e.g., a polar coordinate system). The values may be measured in units of thickness indicative of respective distances from a front to a back of the cataract, or indicative of respective coefficients which include distances from a front to a back of the cataract and density of the cataract.

A portion of the eye scan result 300 is shown in inset 302 which shows four eye thicknesses for respective portions of the eye scan result 300. The top-left quadrant of the inset 302 has a thickness of 5, the top-right quadrant has a thickness of 6, and so on. In some exemplary modes the eye scan result 300 may be represented by any suitable array of values or as a function describing thickness over two-dimensional (or even three-dimensional) space.

Figure 4A:
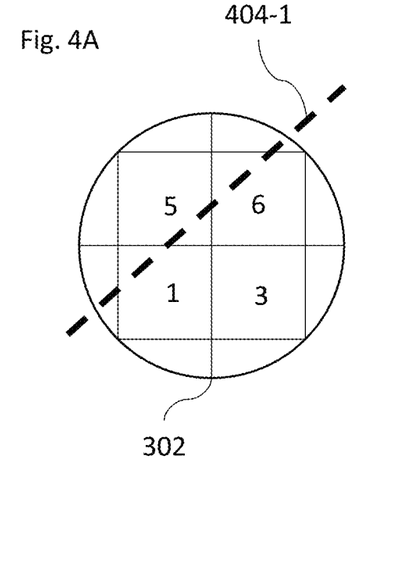
FIGS. 4A-B are schematic views of lines disposed over part of the eye scan result of FIG. 3 to illustrate finding a minimum thickness measurement.
Figure 4B:
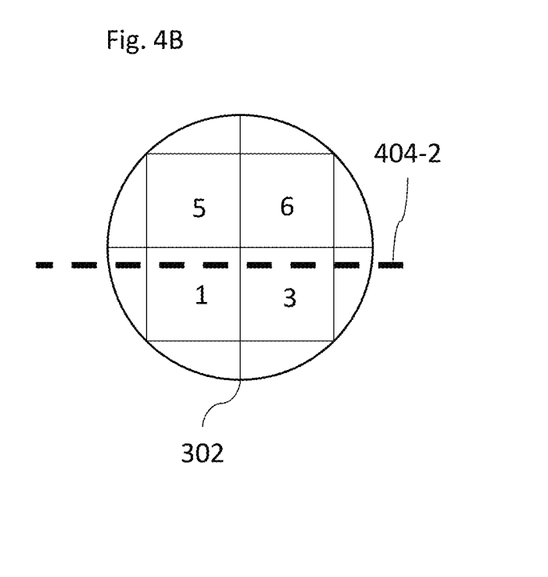

Reference is now made to FIGS. 4A-B, which are schematic views of lines 404 disposed over part of the eye scan result 300 (i.e., shown in the inset 302 of FIG. 3) to illustrate finding a minimum thickness measurement. Reference is also made to FIG. 2.

FIG. 4A shows a line 404-1 traversing quadrants with values 1, 5, and 6, giving a total thickness summation of 12. FIG. 4B shows a line 404-2 traversing quadrants with values 1 and 3, giving a total thickness summation of 4. Therefore, based on the total thickness summation, line 404-2 provides a lower thickness measurement than line 404-1 for that part of the eye scan result 300 shown in FIGS. 4A and 4B.

If the thickness measurement is determined based on a count of the number of values below 4, then line 404-1 gives a value of 1, and line 404-2 gives a value of 2. Therefore, in this case, line 404-2 provides a lower thickness measurement than line 404-1 for that part of the eye scan result 300 shown in FIGS. 4A and 4B.

Any one of the above methods may be applied to the whole eye scan result 300 to find cutlines that are positioned on the eye scan result 300 to provide a minimum thickness measurement. Therefore, the processor 16 is configured to find cutlines through which to cut the cataract 24 into sections responsively to the two-dimensional array of cataract thicknesses (block 204 of FIG. 2). In some exemplary modes, the processor 16 is configured to find the cutlines which provide a minimum thickness measurement responsively to values of the two-dimensional array through which the cutlines traverse. For example, the processor 16 system may find cutlines including the maximum number of thickness values below a given thickness values, e.g., below 2 or 3. In some exemplary modes, the processor 16 is configured to find the cutlines which provide a minimum summation of the values of the two-dimensional array through which the cutlines traverse. For example, if the line passes through thickness values 1, 2, 2, 3, 4, 1 then the thickness measurement is equal to 13.

Figure 5A:
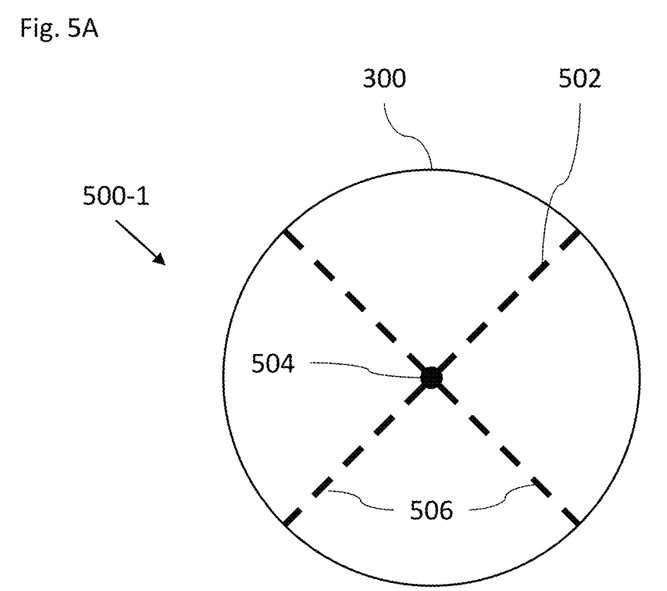
FIGS. 5A-5B are schematic views of different orientations of an arrangement of lines disposed over the eye scan result of FIG. 3 to illustrate finding an orientation of the arrangement of lines providing a minimum thickness measurement.
Figure 5B:
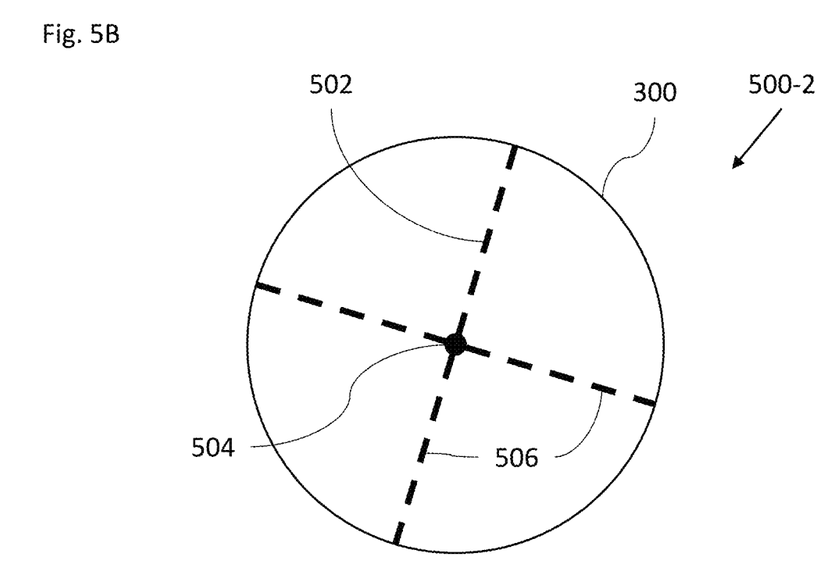

Reference is now made to FIGS. 5A-5B, which are schematic views of different orientations 500 of an arrangement 502 of lines 506 disposed over the eye scan result 300 of FIG. 3 to illustrate finding an orientation of the arrangement 502 of lines 506 providing a minimum thickness measurement. Reference is also made to FIG. 2.

FIG. 5A shows one orientation 500-1 of the arrangement 502 of lines 506 and FIG. 5B shows another orientation 500-2 of the arrangement 502 of lines 506 rotated around a point 504 (e.g., a center of the eye scan result 300). The arrangement 502 is rotated around the point 504 and at each orientation a thickness measurement (e.g., summation of thicknesses) is computed. The orientation providing the minimum thickness measurement is selected to define cutlines for display on the display 20 over the images over the eye 22 and the phacoemulsification probe 18.

Therefore, in some exemplary modes, the processor 16 is configured to rotate the arrangement 502 of lines 506 around the point 504 in the two-dimensional array of the eye scan result 300 to find an orientation 500 of the arrangement 502 which provides the minimum thickness measurement responsively to the values of the two-dimensional array through which the lines 506 of the arrangement 502 traverse (block 206 of FIG. 2). The orientation of the arrangement 502 which provides the minimum thickness measurement defines the cutlines for display. In the example of FIGS. 5A-B, the processor 16 is configured to find the cutlines so that there are four sections being divided by the cutlines. In the example of FIGS. 5A-B, the cutlines intersect and are substantially perpendicular (i.e., within 5 degrees of being exactly perpendicular).

Reference is now made to FIGS. 1 and 2. The processor 16 is configured to render the images (e.g., a live video) of the eye 22 and the phacoemulsification probe 18 with representations 26 of the found cutlines through which to cut the cataract 24 into sections to the display 20 (block 208 of FIG. 2). In some exemplary modes, the processor 16 is configured to render the representations 26 of the found cutlines over the images of the eye 22. In some exemplary modes, the processor 16 is configured to render the representations 26 of the found cutlines with the images of the eye 22 so that the found cutlines are aligned with the images of the eye 22 according to an orientation of the eye 22 within the images. In other words, the representations 26 of the cutlines are rendered on the display 20 such that the orientation of the cutlines with respect to the eye scan result 300 are consistent with the orientation of the eye in the images rendered to the display. The representations 26 may be aligned with the orientation of the eye 22 based on known features of the eye 22 or based on a known relative position between the field of view of the eye scanner 12 and the imaging device 14 or any suitable method.

In practice, some or all of the functions of the processor 16 may be combined in a single physical component or, alternatively, implemented using multiple physical components. These physical components may comprise hard-wired or programmable devices, or a combination of the two. In some examples, at least some of the functions of the processor 16 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

EXAMPLES

Example 1: A phacoemulsification system, comprising: an imaging device configured to capture images of an eye and a phacoemulsification probe; a display; and a processor configured to: receive an eye scan result providing a two-dimensional array of cataract thicknesses of the eye; find cutlines through which to cut the cataract into sections responsively to the two-dimensional array of cataract thicknesses; and render the images of the eye and the phacoemulsification probe with representations of the found cutlines through which to cut the cataract into sections to the display.

Example 2: The system according to example 1, wherein the processor is configured to render the representations of the found cutlines over the images of the eye.

Example 3: The system according to example 1, wherein the processor is configured to render the representations of the found cutlines with the images of the eye so that the found cutlines are aligned with the images of the eye according to an orientation of the eye within the images.

4: The system according to example 1, wherein the processor is configured to find the cutlines which provide a minimum thickness measurement responsively to values of the two-dimensional array through which the cutlines traverse.

Example 5: The system according to example 4, wherein the values are measured in units of thickness indicative of respective distances from a front to a back of the cataract.

Example 6: The system according to example 4, wherein the values are measured in units of thickness indicative of respective coefficients which include distances from a front to a back of the cataract and density of the cataract.

Example 7: The system according to example 4, wherein the processor is configured to find the cutlines which provide a minimum summation of the values of the two-dimensional array through which the cutlines traverse.

Example 8: The system according to example 4, wherein the processor is configured to: rotate an arrangement of lines around a point in the two-dimensional array to find an orientation of the arrangement which provides the minimum thickness measurement responsively to the values of the two-dimensional array through which the lines of the arrangement traverse, the orientation of the arrangement which provides the minimum thickness measurement defining the cutlines.

Example 9: The system according to example 4, wherein the processor is configured to find the cutlines so that there are four sections.

Example 10: The system according to example 9, wherein the cutlines intersect.

Example 11: The system according to example 10, wherein the cutlines are substantially perpendicular.

Example 12: The system according to example 1, wherein the eye scan result is a result derived from an anterior segment optical coherence tomography (AS-OCT) scan.

Example 13: A phacoemulsification method, comprising: capturing images of an eye and a phacoemulsification probe; receiving an eye scan result providing a two-dimensional array of cataract thicknesses of the eye; finding cutlines through which to cut the cataract into sections responsively to the two-dimensional array of cataract thicknesses; and rendering the images of the eye and the phacoemulsification probe with representations of the found cutlines through which to cut the cataract into sections to a display.

Example 14: The method according to example 13, wherein rendering includes rendering the representations of the found cutlines over the images of the eye.

Example 15: The method according to example 13, wherein the rendering includes rendering the representations of the found cutlines with the images of the eye so that the found cutlines are aligned with the images of the eye according to an orientation of the eye within the images.

16: The method according to example 13, wherein the finding includes finding the cutlines which provide a minimum thickness measurement responsively to values of the two-dimensional array through which the cutlines traverse.

Example 17: The system according to example 16, wherein the values are measured in units of thickness indicative of respective distances from a front to a back of the cataract.

Example 18: The system according to example 16, wherein the values are measured in units of thickness indicative of respective coefficients which include distances from a front to a back of the cataract and density of the cataract.

Example 19: The method according to example 16, wherein the finding includes finding the cutlines which provide a minimum summation of the values of the two-dimensional array through which the cutlines traverse.

Example 20: The method according to example 16, further comprising rotating an arrangement of lines around a point in the two-dimensional array to find an orientation of the arrangement which provides the minimum thickness measurement responsively to the values of the two-dimensional array through which the lines of the arrangement traverse, the orientation of the arrangement which provides the minimum thickness measurement defining the cutlines.

Example 21: The method according to example 16, wherein the finding includes finding the cutlines so that there are four sections.

Example 22: The method according to example 21, wherein the cutlines intersect.

Example 23: The method according to example 22, wherein the cutlines are substantially perpendicular.

Example 24: The method according to example 13, wherein the eye scan result is a result derived from an anterior segment optical coherence tomography (AS-OCT) scan.

Example 25: A software product, comprising a non-transient computer-readable medium in which program instructions are stored, which instructions, when read by a central processing unit (CPU), cause the CPU to: receive an eye scan result providing a two-dimensional array of cataract thicknesses of an eye; find cutlines through which to cut the cataract into sections responsively to the two-dimensional array of cataract thicknesses; and render the images of an eye and phacoemulsification probe with representations of the found cutlines through which to cut the cataract into sections to a display.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification system, comprising:
an imaging device configured to capture images of an eye and a phacoemulsification probe;
a display; and
a processor configured to:
receive an eye scan result providing a two-dimensional array of cataract thicknesses of the eye;
find cutlines through which to cut the cataract into sections responsively to the two-dimensional array of cataract thicknesses; and
render the images of the eye and the phacoemulsification probe with representations of the found cutlines through which to cut the cataract into sections to the display.

2. The system according to claim 1, wherein the processor is configured to render the representations of the found cutlines over the images of the eye.

3. The system according to claim 1, wherein the processor is configured to render the representations of the found cutlines with the images of the eye so that the found cutlines are aligned with the images of the eye according to an orientation of the eye within the images.

4. The system according to claim 1, wherein the processor is configured to find the cutlines which provide a minimum thickness measurement responsively to values of the two-dimensional array through which the cutlines traverse.

5. The system according to claim 4, wherein the values are measured in units of thickness indicative of respective distances from a front to a back of the cataract.

6. The system according to claim 4, wherein the values are measured in units of thickness indicative of respective coefficients which include distances from a front to a back of the cataract and density of the cataract.

7. The system according to claim 4, wherein the processor is configured to find the cutlines which provide a minimum summation of the values of the two-dimensional array through which the cutlines traverse.

8. The system according to claim 4, wherein the processor is configured to: rotate an arrangement of lines around a point in the two-dimensional array to find an orientation of the arrangement which provides the minimum thickness measurement responsively to the values of the two-dimensional array through which the lines of the arrangement traverse, the orientation of the arrangement which provides the minimum thickness measurement defining the cutlines.

9. The system according to claim 4, wherein the processor is configured to find the cutlines so that there are four sections.

10. The system according to claim 9, wherein the cutlines intersect.

11. The system according to claim 10, wherein the cutlines are substantially perpendicular.

12. The system according to claim 1, wherein the eye scan result is a result derived from an anterior segment optical coherence tomography (AS-OCT) scan.

13. A phacoemulsification method, comprising:
capturing images of an eye and a phacoemulsification probe;
receiving an eye scan result; providing a two-dimensional array of cataract thicknesses of the eye;
finding cutlines through which to cut the cataract into sections responsively to the two-dimensional array of cataract thicknesses; and
rendering the images of the eye and the phacoemulsification probe with representations of the found cutlines through which to cut the cataract into sections to a display.

14. The method according to claim 13, wherein rendering includes rendering the representations of the found cutlines over the images of the eye.

15. The method according to claim 13, wherein the rendering includes rendering the representations of the found cutlines with the images of the eye so that the found cutlines are aligned with the images of the eye according to an orientation of the eye within the images.

16. The method according to claim 13, wherein the finding includes finding the cutlines which provide a minimum thickness measurement responsively to values of the two-dimensional array through which the cutlines traverse.

17. The method according to claim 16, wherein the values are measured in units of thickness indicative of respective distances from a front to a back of the cataract.

18. The method according to claim 16, wherein the values are measured in units of thickness indicative of respective coefficients which include distances from a front to a back of the cataract and density of the cataract.

19. The method according to claim 16, wherein the finding includes finding the cutlines which provide a minimum summation of the values of the two-dimensional array through which the cutlines traverse.

20. The method according to claim 16, further comprising rotating an arrangement of lines around a point in the two-dimensional array to find an orientation of the arrangement which provides the minimum thickness measurement responsively to the values of the two-dimensional array through which the lines of the arrangement traverse, the orientation of the arrangement which provides the minimum thickness measurement defining the cutlines.

21. The method according to claim 16, wherein the finding includes finding the cutlines so that there are four sections.

22. The method according to claim 21, wherein the cutlines intersect.

23. The method according to claim 22, wherein the cutlines are substantially perpendicular.

24. The method according to claim 13, wherein the eye scan result is a result derived from an anterior segment optical coherence tomography (AS-OCT) scan.

25. A software product, comprising a non-transient computer-readable medium in which program instructions are stored, which instructions, when read by a central processing unit (CPU), cause the CPU to:

receive an eye scan result providing a two-dimensional array of cataract thicknesses of an eye; find cutlines through which to cut the cataract into sections responsively to the two-dimensional array of cataract thicknesses; and render the images of an eye and phacoemulsification probe with representations of the found cutlines through which to cut the cataract into sections to a display.

* * * * *